United States Patent [19]
Larson et al.

[11] Patent Number: 5,401,664
[45] Date of Patent: Mar. 28, 1995

[54] ANALYTICAL METHOD FOR DETERMINING CONCENTRATION OF DECOMPOSITION PRODUCTS IN SOLVENT USED FOR SOLVENT EXTRACTION

[75] Inventors: Richard I. Larson, Wilmington, N.C.; Woodfin V. Ligon, Schenectady, N.Y.; Richard L. Fox, Wilmington, N.C.; Hans Grade, Schenectady, N.Y.

[73] Assignee: General Electric Company, Sane Jose, Calif.

[21] Appl. No.: 74,644

[22] Filed: Jun. 10, 1993

[51] Int. Cl.$^6$ .................. G01N 30/72; G01N 1/00; G01N 37/00
[52] U.S. Cl. .................................. 436/173; 436/8; 436/19; 436/56; 436/103; 436/104; 436/161; 436/174; 436/177
[58] Field of Search .................. 436/8, 19, 56, 100, 436/103, 104, 161, 173, 174, 177

[56] References Cited

U.S. PATENT DOCUMENTS

| | | |
|---|---|---|
| 4,224,031 | 9/1980 | Mee et al. ............... 436/173 |
| 5,036,014 | 7/1991 | Elsohly et al. ............. 436/8 |
| 5,302,758 | 4/1994 | Larson et al. ............. 558/208 |

OTHER PUBLICATIONS

Aldrich Chemical Company Catalog p. 264, 1988.
A. Quayle in "Advances in Mass Spectrometry" J. D. Waldron Ed. 1959, Pergamon Press, New York, 365–383.
C. J. Hardy J. Chromatog. 1964, 13, 372–376.
M. Zinbo et al. Tetrahedron Lett. 1969, 33, 2811–2813.
J. W. Boyden et al. Z. Anal. Chem. 1971, 256, 351–353.
U. Axen et al. Biochem. Biophys. Res. Commun. 1971, 45, 519–525.
W. C. Butts et al. Anal. Chem. 1971, 43, 538–542.
M. Zinbo et al. J. Am. Chem. Soc. 1970, 92, 2105–2114.
P. M. Wiese et al. Anal. Chem. 1972, 44, 2393–2394.
R. H. Getty et al. Anal. Chem. 1977, 49, 1086–1088.
R. Becker et al. Report 1973, KFK-1373, 43 pp.
R. Becker et al. Chem. Abstr. 1974, 81, 85755V.
B. G. Brodda et al. Z. Anal. Chem. 1975, 273, 113–116.
B. S. Middleditch et al. Anal. Lett. 1976, 9, 1031–1034.
Y. C. Lee et al. Anal. Chim. Acta 1979, 106, 373–378.
H. A. James et al. Adv. Mass Spectrom. 1980, 8B, 1429–1435.
Y. Handa et al. J. Chromatog. 1981, 206, 387–391.
Y. Li et al. Chem. Abstr. 1983, 98, 64908h.
C. H. Kuo et al. Analyst 1982, 107, 1190–1194.
T. Ladrielle et al. Radiochem. Radioanal. Lett. 1983, 59, 355–364.
S. Nissen et al. Anal. Biochem. 1990, 188, 17–19.
B. A Tomkins et al. Anal. Chem. 1990, 62, 253–257.
Y. Kuno et al. J. Chromatog. 1991, 537, 489–493.
M. A. Ali et al. Analyst 1991, 116, 1067–1069.
Science and Technology of Tributyl Phosphate, vol. I, Synthesis, Properties, Reactions and Analysis, Schulz et al. (ed.), CRC Press, Inc., Boca Raton, Fla., pp. 268, 269, 276, 278, 280–283, 320, 321 (1984).

Primary Examiner—James C. Housel
Assistant Examiner—Arlen Soderquist
Attorney, Agent, or Firm—J. E. McGinness

[57] ABSTRACT

A safe analytical technique for determining the concentration amount of dibutyl and monobutyl phosphate degradation products in the TBP-dodecane solvent used in solvent extraction processes. This method of chemical analysis eliminates the use of diazomethane, which is toxic and explosive, thereby providing a safer laboratory technique for routine analyses required to monitor production solvent extraction processes. The solvent sample to be analyzed is spiked with mass labelled, deuterated dibutyl and monobutyl phosphates, which act as internal standards. After adding a silylating agent, bistrimethylsilyltrifluoracetamide, the sample is injected into a gas chromatograph/mass spectrometer, which measures the ratio between the labelled internal standard and the naturally occurring material to obtain a quantitative result.

2 Claims, 3 Drawing Sheets

ANALYTICAL METHOD FOR DETERMINING CONCENTRATION OF DECOMPOSITION PRODUCTS IN SOLVENT USED FOR SOLVENT EXTRACTION

FIELD OF THE INVENTION

This invention relates to methods for determining the concentration of a compound in a solution by gas chromatography/mass spectrometry. In particular, it relates to a method for determining the concentrations of decomposition products of tributyl phosphate which are present in a solvent used in a solvent extraction process to recover uranium from waste or spent material.

BACKGROUND OF THE INVENTION

The solvent extraction process for recovering uranium consists of a sequence of chemical steps or operations performed on scrap material or spent fuel. First, the scrap material or spent fuel containing uranium compounds is treated with an aqueous solution of nitric acid ($HNO_3$), whereby the uranium is dissolved to produce uranyl nitrate ($UO_2(NO_3)_2$) and other acid-soluble components in an aqueous phase. This aqueous phase is passed down a solvent extraction column while an organic phase of tri-n-butyl phosphate (TBP) in an organic diluent of a paraffinic mixture, such as dodecane, is passed up through the extraction column in countercurrent flow with the aqueous phase. The soluble uranium compounds of the aqueous phase are extracted therefrom by the organic phase and combined with the TBP. The uranium is thus separated from the acid-soluble raffinate contaminants remaining in the aqueous phase and carried by the organic phase from the extraction column. The aqueous and organic phases exit at opposite ends of the extraction column.

The organic phase effluent from the extraction column is then passed up through a stripping column while water is passed down through the stripping column in countercurrent flow with the organic phase. The water releases the uranium from the TBP of the organic phase, whereby it is transferred to and carried within the aqueous phase. The aqueous and organic phases exit at opposite ends of the stripping column, the aqueous phase containing the recovered uranium compounds separated from contaminants. The organic phase is then recycled back through the extraction column. Typically the procedure is carried out with a continuous flow of all components through the system comprising the extraction and stripping columns. The desired product of the solvent extraction process is a high-purity aqueous phase effluent containing virtually all the uranium of the initial waste fed into the system.

Ionizing radiation, elevated temperature and acids cause decomposition of TBP in all of the solvent extraction processes that separate heavy metals, such as uranium, plutonium, thorium and gadolinium. The decomposition products prevent separation of the desired products uranium and plutonium from unwanted wastes, such as gadolinium, zirconium, and fission products.

The acid feed to solvent extraction includes deesterification (dealkylation and hydrolysis) reactions producing dibutyl phosphoric acid (DBP), monobutyl phosphoric acid (MBP), phosphoric acid and butyl alcohol. The sequence of deesterification reactions are summarized below:

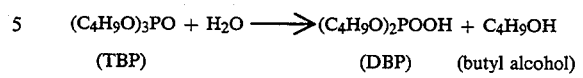

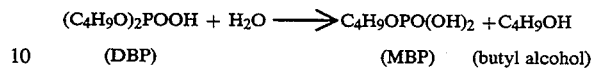

Dibutyl phosphoric acid (DBP) complexes with uranium, zirconium, and gadolinium, forming compounds soluble in TBP and its solution in hydrocarbon diluents (dodecane or kerosene). This results in a lower gadolinium or zirconium decontamination factor, and an increase in uranium losses in the raffinate, or aqueous waste, produced by the solvent extraction process.

Gas chromatography is the standard analytical method for determining the small quantities of DBP and MBP in TBP and TBP-diluent solutions. To measure these degradation products, DBP and MBP are converted to the more volatile methyl esters, namely, $CH_3DBP$ and $(CH_3)_2MBP$.

Methylation prevents the problems of migration of the low-volatility acids through the packed columns of the gas chromatograph and of their dissociation within the columns. The methylating agent commonly used is diazomethane ($CH_2N_2$), which is both explosive and toxic.

SUMMARY OF THE INVENTION

The present invention is an improved analytical technique for determining the concentrations of dibutyl and monobutyl phosphates in solvent used for solvent extraction. This method of chemical analysis eliminates the use of diazomethane, which is toxic and explosive, thereby providing a safer laboratory technique for routine analyses required to monitor production solvent extraction processes.

In accordance with the technique of the invention, the solvent sample to be analyzed is spiked with mass-labelled, deuterated dibutyl and monobutyl phosphates, which act as internal standards. After adding a silylating agent, bistrimethylsilyltrifluoracetamide (BSTFA), the sample is injected into a gas chromatograph/mass spectrometer, which measures the ratio between the labelled internal standard and the naturally occurring material to obtain a quantitative result. The concentration of the decomposition product of interest is determined using this quantitative result and a calibration curve.

The method of the invention can be used to measure the level of decomposition products of TBP in the solvent. If the measured level exceeds a prescribed threshold, the solvent can be treated to reduce the level of decomposition products. This enables improved performance of solvent extraction processes used to separate heavy metals, such as uranium, plutonium, thorium and fission products, by increasing the separation efficiency for uranium, thorium, and gadolinium and also by increasing the total throughput of the solvent extraction columns.

DETAILED DESCRIPTION OF THE PREFERRED EMBODIMENT

The basis for the analytical technique of the invention are mass-labelled internal standards of deuterated dibutyl and monobutyl phosphates. These are added to the sample of TBP-dodecane being measured. Both the deuterated and undeuterated dibutyl and monobutyl phosphoric acids are then extracted with water, eliminating most of the TBP and dodecane. After drying, the solid residue is treated with a silylating agent, e.g., BSTFA. This mixture is then analyzed using gas chromatography/mass spectrometry (GC/MS).

Treatment with BSTFA converts the acid phosphates into trimethylsilyl esters, according to the following reactions:

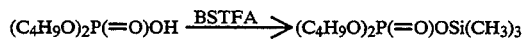

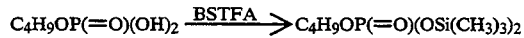

Figure 1:
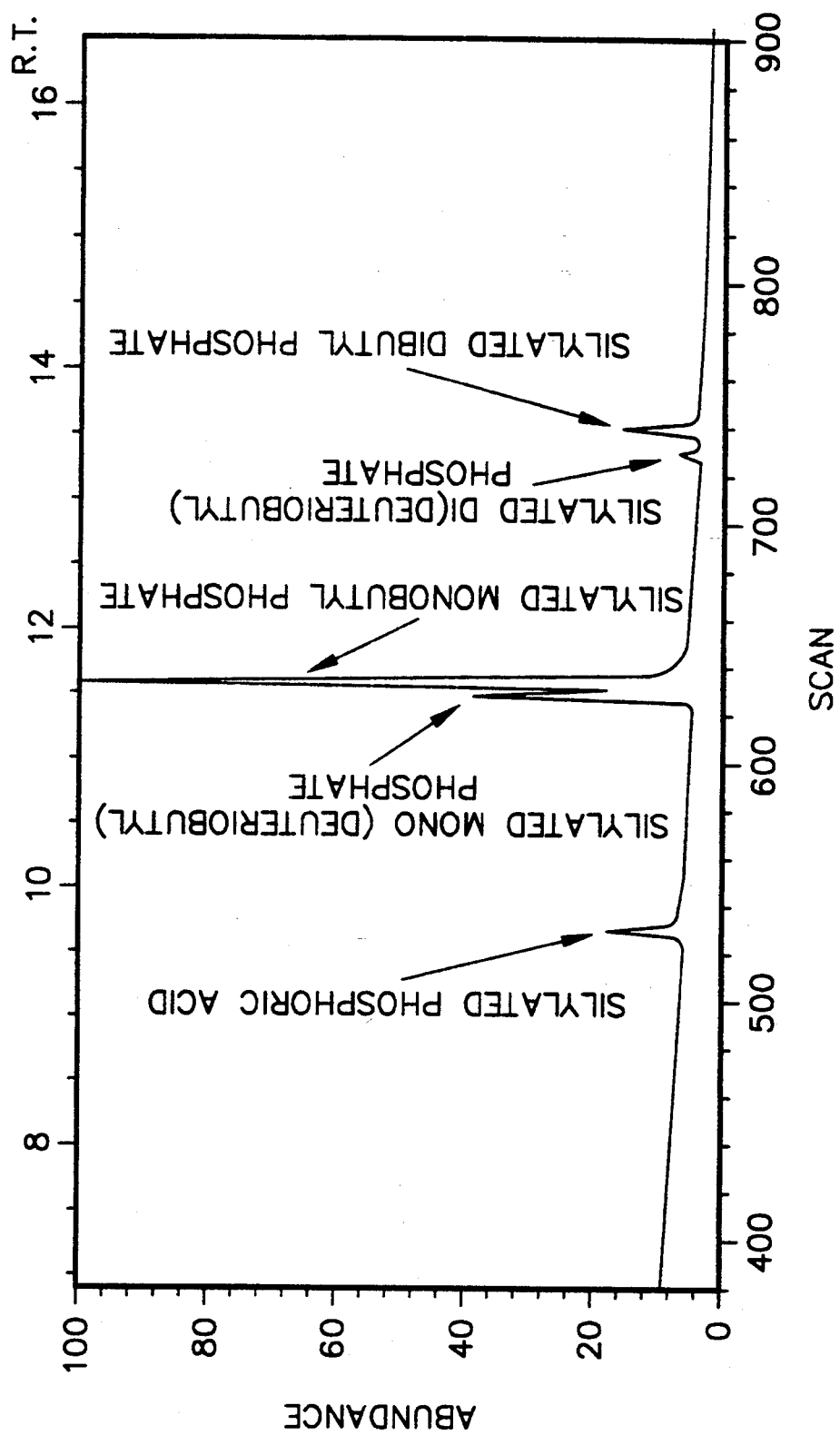
FIG. 1 shows an exemplary chromatogram of a sample of the derivatized solution in accordance with the method of the invention.
Figure 2:
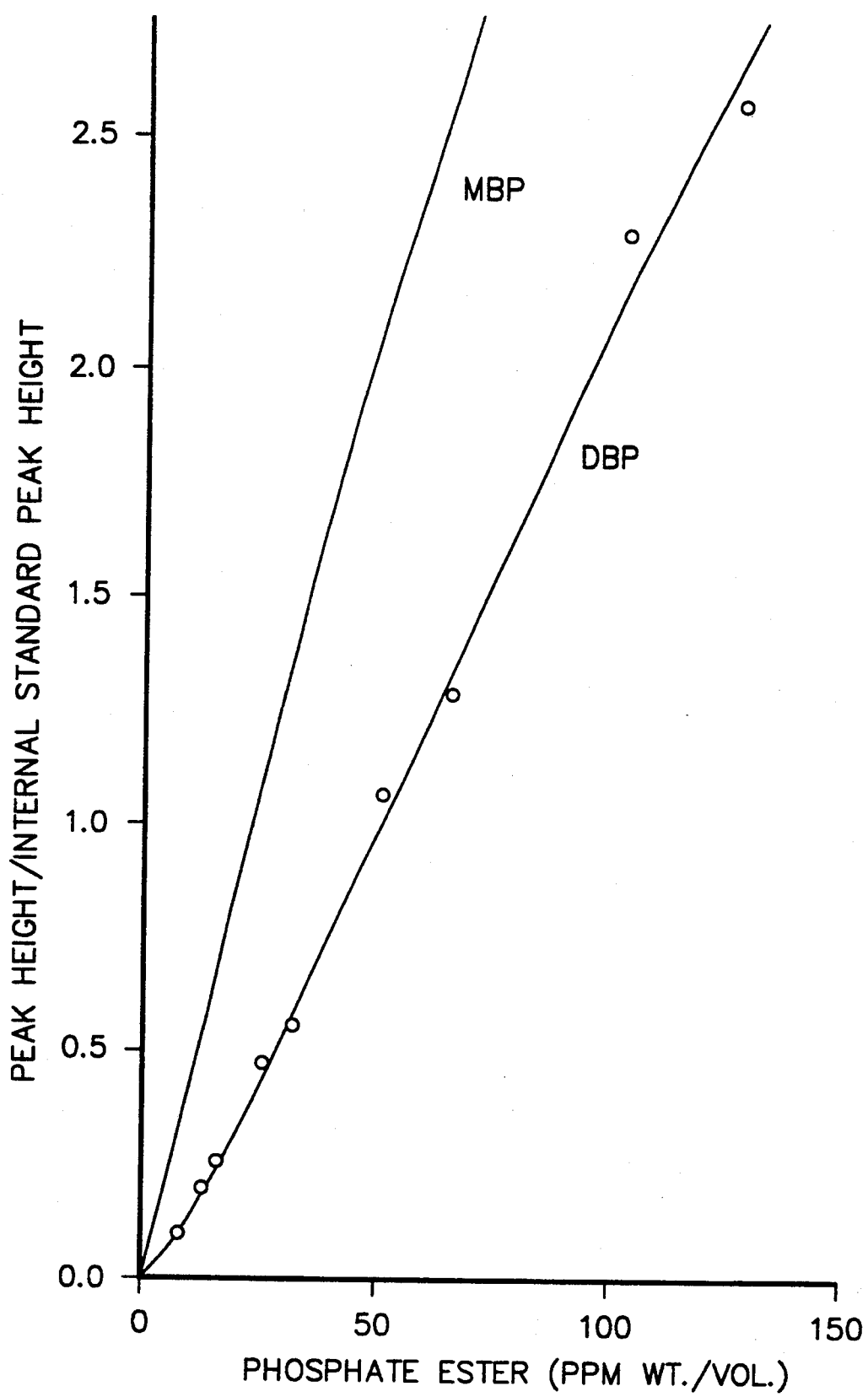
FIG. 2 is a graph showing an empirical calibration plot for the analysis of dibutyl phosphoric acid and a computed calibration plot for monobutyl phosphoric acid analysis in accordance with the method of the invention.

Aliquots of the derivatized solutions are then injected into the gas chromatograph/mass spectrometer. FIG. 1 shows an example of the chromatogram obtained on these samples. FIG. 2 shows a typical butyl phosphate ester analysis calibration plot and the corresponding data points: (□) data; (+) linear regression; and (O) rerun.

The method in accordance with the invention requires a deuterated internal standard which must be synthesized. The first step in the synthesis of the deuterated internal standard is to combine deuterated butanol ($C_4D_9OH$) with phosphorus oxychloride ($POCl_3$) in methylene chloride ($CH_2Cl_2$) and pyridine. The deuterated butanol reacts with phosphorus oxychloride and water to produce deuterated MBP (d-MBP), deuterated DBP (d-DBP) and deuterated TBP in accordance with the following reaction:

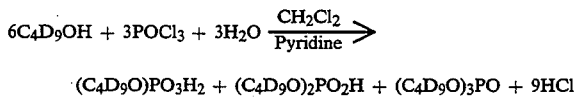

The reactants were combined in a small separatory funnel in the following order: (1) 12.5 ml methylene chloride; (2) 625 μl deuterated butanol; (3) 1900 μl pyridine; and (4) 625 μl phosphorus oxychloride added using a 1-ml syringe. This combination was swirled and then allowed to stand for 10 min.

The reaction was worked up using the following steps in the order indicated: (1) add 12.5 ml of water; (2) insert a stopper in the separatory funnel and shake the funnel vigorously for 2-3 min, being sure to relieve the pressure inside the funnel frequently; (3) allow the layers in the separatory funnel to separate; (4) carefully separate the methylene chloride (bottom) layer; (5) add 12.5 ml of fresh methylene chloride to the separatory funnel and again shake the funnel vigorously; (6) again allow the layers in the separatory funnel to separate; (7) again separate the methylene chloride (bottom) layer and combine it with the first bottom layer; (8) evaporate the combined bottom layers to dryness using a slow stream of dry nitrogen gas; (9) treat the residue from step (8) with 50 ml of diethyl ether (Note: Only part of the residue will dissolve.); (10) decant the ether solution and then treat the residue with a second 50 ml of diethyl ether; (11) decant the second ether solution and combine it with the first ether solution; and (12) evaporate the combined ether solutions to dryness using a stream of dry nitrogen gas.

The resulting deuterated MBP and deuterated DBP can be used to measure the amounts of MBP and DBP in a TBP or TBP-diluent solution. The method of preparing the phosphate samples for GC/MS analysis in accordance with the invention comprises the following steps:

(1) Ten microliters of an internal standard solution having a d-DBP concentration of 7.5 μg/μl and a d-MBP concentration of 9.8 μg/μl are injected into a 1-ml conical vial.

(2) The solvent from the internal standard solution (methylene chloride) is evaporated with nitrogen.

(3) One hundred and fifty microliters of water are added to the conical vial and mixed thoroughly for 30 sec using a vortex mixer.

(4) About 350 mg of TBP sample are weighed into the vial and the resulting two-phase solution is agitated with a vortex mixer for 1.5 min.

(5) A syringe is used to transfer the aqueous (bottom) layer to a second conical vial. Care must be taken that the top layer is not sampled.

(6) About 0.5 ml of hexane is added to the second vial containing the aqueous layer and this two-phase system is agitated for 30 sec with a vortex mixer.

(7) A syringe is used to transfer the aqueous (bottom) layer to a third vial.

(8) The water is removed from the third vial using a slow stream of dry nitrogen gas.

(9) After drying, 100 μl of BSTFA is added from an ampule to the dry residue produced by step (8). This mixture is allowed to stand for 30 min at room temperature before analysis.

(10) The solution resulting from step (9) is analyzed by GC/MS using a J&W Scientific model DB-1 capillary column isothermal at 90° C. for 1.5 min and then programmed to rise in temperature from 90° C. to 270° C. at a rate of 8° C./min. The temperature of the injector port was 195° C. The mass spectra were acquired as shown in FIG. 1 and were quantified using the calibration plot shown in FIG. 2.

Although 350 mg of TBP were used in the above example, the amount of TBP is dependent on the sensitivity of the gas chromatograph/mass spectrometer being used. For example, if equipment more sensitive were used, the amount of TBP can be decreased, e.g., by a factor of 10.

Figure 3:
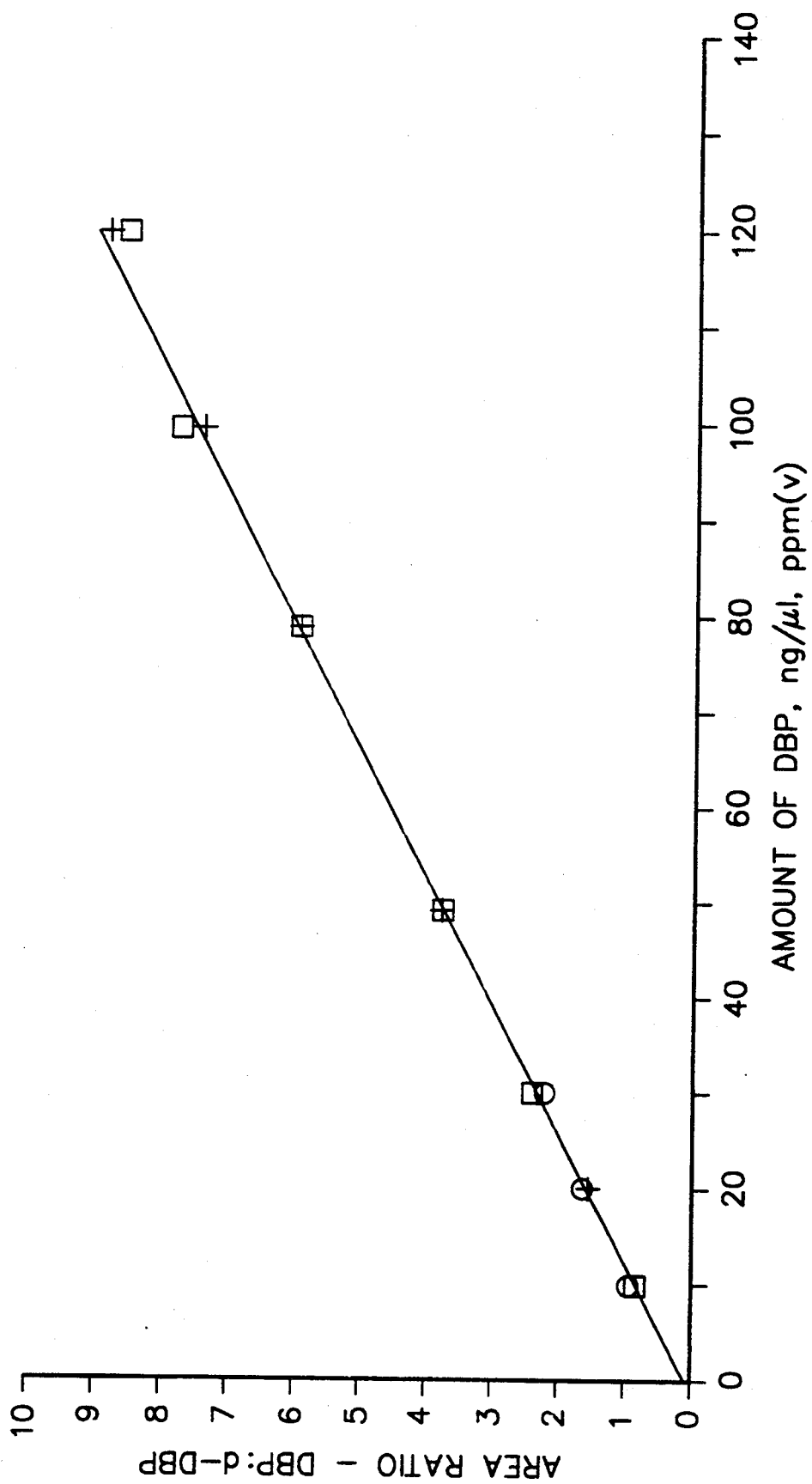
FIG. 3 is a graph showing a calibration plot for dibutyl phosphoric acid analysis obtained in accordance with the method of the invention.

The analytical method for calibrating the equipment in accordance with the invention will be described in detail with reference to the calibration plot of FIG. 3. Dibutyl phosphate, 97.6% by titration, is introduced in different volumes, together with the mass-labelled, fully deuterated dibutyl phosphate, to provide the calibration curve in FIG. 3. Two standard solutions, unlabelled O-standard and mass-labelled D-standard, are prepared according to the method outlined below.

An unlabelled solution of dibutyl phosphate (97.6%) is prepared in a solution of methylene chloride solvent at a concentration of about 0.1 mg/ml. The mass-labelled, deuterated dibutyl phosphate is combined with methylene chloride solvent at a concentration of 0.3 to 3.0 mg/ml. After preparing the O-standard and D-standard solutions, different volumes of the starting solution are prepared as shown in Table 1.

TABLE 1

| Vial No. | O-Standard ($\mu$l) | D-Standard ($\mu$l) |
| --- | --- | --- |
| 1 | 10 | 10 |
| 2 | 30 | 10 |
| 3 | 50 | 10 |
| 4 | 80 | 10 |
| 5 | 100 | 10 |
| 6 | 120 | 10 |

The methylene chloride is evaporated and an excess of BSTFA is added at about 100 $\mu$l. Table 2 shows the resulting concentrations used for calibration.

TABLE 2

| Vial No. | DBP Concentration (ng/$\mu$l) | d-DBP Concentration (ng/$\mu$l) |
| --- | --- | --- |
| 1 | 10 | 10 |
| 2 | 30 | 10 |
| 3 | 50 | 10 |
| 4 | 80 | 10 |
| 5 | 100 | 10 |
| 6 | 120 | 10 |

Because of the difficulty in resolving mass-labelled and unlabelled compounds chromatographically, the reconstructed ion chromatograms for DBP and d-DBP masses 171 and 174 are used for calibration. Masses 243 and 245 correspond to MBP and d-MBP.

The amount of DBP in a sample is determined from the ratio of the peak areas of DBP and d-DBP. Knowing the weight of the DBP in the sample and using the calibration curve of FIG. 3, the DBP concentration in the sample can be determined. Similarly, the concentration of MBP in a sample can be determined from the weight of MBP in the sample and a suitable calibration curve (see FIG. 2).

Four samples were prepared to compare the standard method of measurement involving diazomethane and GC with the analytical technique based on a deuterated internal standard. A known quantity of DBP and MBP was added to Sample Nos. 2 and 4. Sample Nos. 1 and 3 had unknown levels of contaminants. Table 3 compares the results of the respective methods.

TABLE 3

| Sample No. | Standard Method | | New Analytical Method | |
| --- | --- | --- | --- | --- |
| | DBP (ppm) | MBP (ppm) | DBP (ppm) | MBP (ppm) |
| 1 | <5 | <5 | 7 | ND |
| | | | 7 | 0.2 |
| 2 | 90 | 120 | 94 | 112 |
| | | | 94 | 118 |
| | | | 99 | 118 |
| | | | 96 | 101 |
| | | | 90 | 94 |
| 3 | <5 | <5 | 7 | 0.3 |
| 4 | 100 | 110 | 98 | 132 |
| | | | 92 | 118 |

Good agreement is observed between the results for the two techniques. Consequently, the technique of the invention provides a safe analytical method for determining the operating performance of a production solvent extraction system.

The method of the invention has been described in terms of specific steps for the purpose of illustration. It will be apparent to practitioners skilled in the art of gas chromatography/mass spectrometry that these steps may be varied or modified without departing from the broad concept of the invention. All such variations and modifications are intended to be encompassed by the claims appended hereto.

We claim:

1. A method for determining the concentration of an undeuterated compound, selected from the group consisting of dibutyl phosphoric acid and monobutyl phosphoric acid, in a sample of a solution by gas chromatography/mass spectrometry using an internal standard, comprising the steps of:

placing a predetermined volume of an internal standard solution having a predetermined concentration of a deuterated version of said undeuterated compound dissolved in a first solvent into a first vial;

evaporating said first solvent to form a residue;

mixing said residue with water to form an aqueous mixture;

adding a predetermined weight of said sample of said solution to said aqueous mixture to form a first two-phase solution with an aqueous bottom layer and then agitating said first two-phase solution;

placing said aqueous bottom layer of said first two-phase solution in a second vial;

adding a predetermined volume of a second solvent to said second vial to form a second two-phase solution with an aqueous bottom layer and then agitating said second two-phase solution;

placing the aqueous bottom layer of said second two-phase solution in a third vial;

evaporating the water from said third vial to form a dry residue;

adding a predetermined volume of a silylating agent to said dry residue to form a silylated product; and performing gas chromatography/mass spectrometry on said silylated product.

2. A method for determining the concentration of an undeuterated compound in a sample of a solution by gas chromatography/mass spectrometry using an internal standard, said undeuterated compound having a first chemical formula, said internal standard being a deuterated compound having a second chemical formula, the only difference between said first and second chemical formulas being that a predetermined number of hydrogen atoms in said undeuterated compound are replaced by an equal number of deuterium atoms to form said deuterated compound, wherein said undeuterated compound is a phosphoric acid taken from the group consisting of dibutyl phosphoric acid and monobutylphosphoric acid, comprising the steps of:

forming a calibration curve showing the standard correlation between the mass spectra of said undeuterated and deuterated compounds for known concentrations of said undeuterated compound;

forming a predetermined volume of a solution comprising an unknown weight of said undeuterated compound, a known weight of said deuterated compound, and a silylating agent;

producing a graph of the mass spectra corresponding to said solution using gas chromatography/mass spectrometry;

determining the ratio of the area under a first peak on said graph corresponding to said undeuterated compound to the area under a second peak on said graph corresponding to said deuterated compound; and determining the concentration of said undeuterated compound in said predetermined volume of said solution using said determined ratio and said calibration curve, wherein said step of forming a predetermined volume of a solution comprising an unknown weight of said undeuterated compound, a known weight of said deuterated compound, and a silylating agent comprises the steps of:

placing a predetermined volume of an internal standard solution having a predetermined concentration of said deuterated compound dissolved in a first solvent into a first vial;

evaporating said first solvent to form a residue;

mixing said residue with water to form an aqueous mixture;

adding a predetermined weight of a sample of a solution comprising said undeuterated compound to said aqueous mixture to form a first two-phase solution and then agitating said first two-phase solution;

placing said aqueous bottom layer of said first two-phase solution in a second vial;

adding a predetermined volume of a second solvent to said sample of said aqueous layer to form a second two-phase solution and then agitating said second two-phase solution;

placing the aqueous bottom layer of said second two-phase solution in a third vial;

evaporating the water from said third vial to form a dry residue; and adding a predetermined volume of a silylating agent to said dry residue.

* * * * *